United States Patent [19]

Wulfert et al.

[11] Patent Number: 5,447,952
[45] Date of Patent: Sep. 5, 1995

[54] TREATMENT OF ANXIETY WITH THE AID OF (S)-(−)-α-ETHYL-2-OXO-1-PYRROLIDINEACETAMIDE

[75] Inventors: Ernst Wulfert; Jean Gobert, both of Brussels; Alma Gower, Braine-l'Alleud; Eric Cossement, Brussels, all of Belgium

[73] Assignee: U C B S.A., Brussels, Belgium

[21] Appl. No.: 309,186

[22] Filed: Sep. 20, 1994

[30] Foreign Application Priority Data

Sep. 24, 1993 [GB] United Kingdom ............... 9319732

[51] Int. Cl.⁶ .................................... A61K 31/40
[52] U.S. Cl. .................................... 514/424
[58] Field of Search ........................ 514/424

[56] References Cited

U.S. PATENT DOCUMENTS 4,696,943  9/1987  Gobert et al. .
4,837,223  6/1989  Gobert et al. .
4,943,639  7/1990  Gobert et al. .

FOREIGN PATENT DOCUMENTS 0162036 11/1985 European Pat. Off. .

OTHER PUBLICATIONS

Gower et al., Eur. J.Pharmacol. (Netherlands), No. 10, 1992, vol. 222, No. 2–3, pp. 193–203.
"UCB L059, A Novel Anti–Convulsant Drug: Pharmacological Profile In Animals" [Published erratum appears in Eur J Pharmacol 1993 Jan. 19; 230(3):389].
Loscher et al., Eur. J. Pharmacol (Netherlands), Mar. 2, 1993, vol. 232, No. 2≧3, pp. 147–158.
"Profile of UCB L059, A Novel Anticonvulsant Drug, In Models of Partial and Generalized Epilepsy In Mice and Rats" (1993).
Wulfert et al., Psychopharmacol Bull (United States), 1989, vol. 25, No. 3, pp. 498–502.
"Facilitation of Calcium–Dependent Cholinergic Function By UCB L059, a New 'Second Generation' Nootropic Agent" (1992).
File et al., N. Affect Disord (Netherlands), Dec. 1979, vol. 1, No. 4, pp. 227–235 "Evidence That Piracetam Has An anxiolytic Action".

*Primary Examiner*—Raymond Henley, III
*Assistant Examiner*—William R. A. Jarvis
*Attorney, Agent, or Firm*—Wenderoth, Lind & Ponack

[57] ABSTRACT

A method is disclosed for the treatment of anxiety in a patient in need thereof, by administering to said patient an effective amount of (S)-(−)-α-ethyl-2-oxo-1-pyrrolidineacetamide of the formula

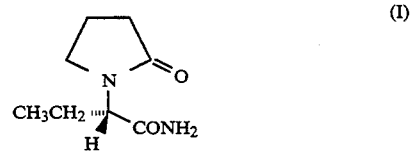

(I)

6 Claims, No Drawings

TREATMENT OF ANXIETY WITH THE AID OF (S)-(−)-α-ETHYL-2-OXO-1-PYRROLIDINEACETAMIDE

The present invention relates to the use of (S)-(−)-α-ethyl-2-oxo-1-pyrrolidineacetamide for the treatment of anxiety.

The use of levorotatory (S)-α-ethyl-2-oxo-1-pyrrolidineacetamide as a protective agent for the treatment and the prevention of hypoxic and ischemic type aggressions of the central nervous system is disclosed in U.S. Pat. Nos. 4,696,943, 4,837,223 and 4,943,639, all three assigned to the assignee of the present invention. This compound is also effective in the treatment of epilepsy, a therapeutic indication for which it has been demonstrated that its dextrorotatory enantiomer (R)-(+)-α-ethyl-2-oxo-1-pyrrolidineacetamide completely lacks activity (A. J. GOWER et al., Eur. J. Pharmacol., 222, (1992), 193–203). No disclosure of the use of levorotatory (S)-α-ethyl-2-oxo-1-pyrrolidineacetamide for the treatment of anxiety is known, however.

In the above-mentioned U.S. Pat. Nos. 4,696,943, 4,837,223 and 4,943,639, processes for preparing (S)-(−)-α-ethyl-2-oxo-1-pyrrolidineacetamide are also described. These processes involve the synthesis of a starting reactant obtained by resolution of the corresponding racemate. In British Patent No. 2,225,322, also assigned to the assignee of the present invention, a process for the preparation of this compound is described, which offers the advantage of using a naturally occurring amino acid with the desired stereochemical configuration as the starting material. This process thus avoids tedious separation of the enantiomers.

Continuing research work in this field, we have now found that (S)-(−)-α-ethyl-2-oxo-1-pyrrolidineacetamide possesses anxiolytic properties of considerable therapeutic interest.

Moreover, this anxiolytic activity could not be found for the dextrorotatory enantiomer, (R)-(+)-α-ethyl-2-oxo-1-pyrrolidineacetamide.

Thus, the present invention relates to a new and useful method for the treatment of anxiety in a patient in need thereof, which comprises administering to said patient an effective amount of (S)-(−)-α-ethyl-2-oxo-1pyrrolidineacetamide of the formula

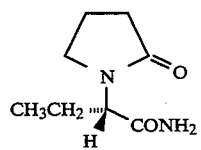
(I)

The anxiolytic activity of (S)-(−)-α-ethyl-2-oxo-1-pyrrolidineacetamide is particularly pronounced in pharmacological situations in which the initial emotional state has been exacerbated, for example by choosing particularly sensitive or aged animals, or by using experimental conditions that involve the anticipation of an aversive stimulus.

The relation between anxiolytic activity of the compound of the formula I and the intensity of the initial emotional state, suggests that the therapeutic application of this compound will preferably be directed towards the treatment of pathological anxiety states. This selectivity clearly distinguishes the compound used according to the invention from known anxiolytic medicaments of the benzodiazepine type, and offers an important advantage over these other classes of products, which act without distinguishing between an anxious animal and a normal animal. In the latter case, the anxiolytic activity is accompanied by disinhibition of the normal general behavior, thereby inducing an inadequate adaptative response in healthy subjects, that should be avoided. In this context, (S)-(−)-α-ethyl-2-oxo-1-pyrrolidineacetamide facilitates recovery and return to a more normal situation from pathological anxiety states caused by disorders of a neuroendocrine origin produced by stress in aged subjects, as opposed to the benzodiazepines which do not favor this recovery. Contrary to benzodiazepines, for which amnesia and neuromotor disturbances such as ataxia, muscular relaxation and sedation are well known and undesirable side-effects (J. H. WOODS et al., Pharmacol. Rev.,39 (1987), 251–419), therapeutic doses of (S)-(−)-α-ethyl-2-oxo-1-pyrrolidineacetamide do not produce the slightest harmful effect on memory and do not cause awkward neuromotor effects. Indeed, there is a large safety margin between the anxiolytic doses and the neurotoxic or sedative doses in animals (A. J. GOWER et al., loc.cit.).

Furthermore, (S)-(−)-α-ethyl-2-oxo-1-pyrrolidineacetamide also reduces the anxiety induced by the withdrawal from chronic administration of benzodiazepines.

The result of this unexpected range of properties is that the use of (S)-(−)-α-ethyl-2-oxo-1-pyrrolidineacetamide is particularly suited in the treatment of anxiety states, such as general anxiety, panic, agoraphobia, social phobia, obsessive-compulsive disorders, anxiety due to acute posttraumatic stress, feelings of impending danger, absence of tonus, fear and tension, which are sometimes accompanied by physiological symptoms such as tachycardia, dyspnea, sweating, trembling, weakness and fatigue (International Statistical Classification of Diseases and Related Health Problems—Tenth Revision, Vol. 1, World Health Organization, Geneva, 1992).

The present invention requires administration of a dose of the compound of the formula I effective to treat anxiety. The dose required according to the present invention should be sufficiently high to permit the relief of anxiety. Pharmaceutical compositions containing the compound of the formula I may be administered, for example, orally or parenterally, i.e. intravenously, intramuscularly and subcutaneously.

The pharmaceutical compositions which can be used for oral administration may be solid or liquid, for example, in the form of tablets, pills, dragees, gelatine capsules, solutions, syrups, and the like.

For this purpose, the active compound can be mixed with an inert diluent or a pharmaceutically acceptable non-toxic carrier, such as for example starch or lactose. Optionally, these pharmaceutical compositions can also contain a binder such as microcrystalline cellulose, gum tragacanth or gelatine, a disintegrating agent such as alginic acid, a lubricant such as magnesium stearate, a glidant such as colloidal silicon dioxide, a sweetening agent such as sucrose or saccharin, a coloring agent or a flavoring agent such as peppermint or methyl salicylate. These compositions also include compositions that allow controlled release of the active substance.

The pharmaceutical compositions which can be used for parenteral administration are the pharmaceutical forms known for this mode of administration, for example, aqueous or oily solutions or suspensions generally contained in ampules, disposable syringes, vials made of glass or plastic, or infusion containers.

Besides the active compound, these solutions or suspensions can optionally also contain a sterile diluent such as water for injection, physiologic saline solution, oils, polyethylene glycols, glycerine, propylene glycol or other synthetic solvents, antibacterial agents such as benzyl alcohol, antioxidants such as ascorbic acid or sodium bisulfite, chelating agents such as ethylenediaminetetraacetic acid, buffers such as acetates, citrates or phosphates and agents for adjusting the osmolality such as sodium chloride or dextrose.

These pharmaceutical forms can be prepared according to conventional methods used by pharmacists.

The percentage of active compound in the pharmaceutical compositions can vary within very wide concentration limits and depends on a variety of factors such as the sex, age, weight and medical condition of the patient, as well as the method of administration. Thus the amount of active compound in compositions intended for oral administration, is at least 0.5% by weight, and can reach 80% by weight with respect to the weight of the composition. In the preferred oral compositions, the dosage unit is between 50 mg and 1000 mg of active compound.

In compositions intended for parenteral administration, the amount of active compound present is at least 0.5% by weight and can reach 33% by weight of the composition. In the preferred parenteral compositions, the dosage unit is between 1 mg and 200 mg of active compound.

As regards the daily dosage, this can vary within a wide range of dosage units and is preferably between 5 and 70 mg/kg. An average dose of 250 mg, twice a day, has proved to be effective in relief of anxiety in man. It is to be understood, however, that the specific doses can be adapted for particular cases, depending on individual need, at the discretion of the responsible physician. The above-mentioned dosages are given exemplary only and by no means limit the scope of practice of the invention.

As non-limiting examples of compositions containing (S)-(−)-α-ethyl-2-oxo-1-pyrrolidineacetamide, which can be administered orally, four compositions are given hereinafter for white and opaque gelatine capsules:

|  | Number of the capsules | | | |
| --- | --- | --- | --- | --- |
|  | 1 | 1 | 1 | 0 |
| Compound I | 62.5 mg | 125 mg | 250 mg | 500 mg |
| Lactose | 362.5 mg | 264 mg | 89 mg | 50 mg |
| Magnesium stearate | 1 mg | 1 mg | 1 mg | 2 mg |

The efficacy of (S)-(−)-α-ethyl-2-oxo-1-pyrrolidineacetamide for the treatment of anxiety is demonstrated by its activity in the following pharmacological tests performed on animals, using standard tests, which are recognized for their capacity to demonstrate the anxiolytic activity of new compounds.

Anxiety can exist in different physiological and pathological forms. The heterogeneous nature of anxiety disorders is clinically accepted in the same way that it is accepted that various anxiety tests, performed on animals and based on behavioral changes are sensitive to different types of anxiety (S. E. FILE, "Animal models of anxiety" in "Biological Psychiatry", Vol. 2, G. Racagui et al. (eds), Excerpta Medica, Amsterdam, (1991), p. 596–599).

However, to be sure that a given behavioral test actually permits to detect anxiolytic activity, the latter must also be confirmed by clinical tests. A test in man has enabled to confirm the therapeutic activity of (S)- (−)-α-ethyl-2-oxo-1-pyrrolidineacetamide for the treatment of various types of anxiety.

1. Hole-board Test (Exploratory Activity)

The hole-board test offers a simple method for studying the behavior of a rodent and for measuring the response of an animal to an unfamiliar environment. This reaction, known as the "exploratory behavior", relates both to the curiosity of the animal and to its natural fight-or-flight reaction and is influenced by psychoactive drugs. In particular, this method has proved useful in predicting the potential anxiolytic activity of benzodiazepines (N. A. NOLAN and M. W. PARKES, Psychopharmacologia (Berl.) 29, (1973), 277–288). Using the methodology of J. R. BOISSIER and P. SIMON (Arch. Int. Pharmacodyn. 147, (1964), 372–387), the test consists of placing a mouse in the center of a square board, perforated by 16 regularly spaced holes, and counting the number of times the animal dips its head into a hole during a five-minute exploration period. Three genetically distinct strains of mice are used in this test; a normal strain of NMRI mice and two strains which are emotionally more sensitive, one being prone to audiogenic seizure (Dilute Brown Agouti-derived (DBA-derived)), and the other having the normal fight-or-flight reaction blocked by fear (C57 Black Mice strain).

The activities of (S)-(−)-α-ethyl-2-oxo-1-pyrrolidineacetamide (compound I), of its dextrorotatory enantiomer (R)-(+)-α-ethyl-2-oxo-1-pyrrolidineacetamide (compound II) and of diazepam are compared on these three strains.

The compounds are administered to the animals by intraperitoneal injection (10 ml/kg of mouse) 30 minutes before exposure to the board. Animals in the control group receive the carrier only.

Table I shows the mean of the number of holes explored per group of 16 animals (X±SEM) for each of the strains (control and treated animals) at the doses indicated (SEM: Standard Deviation from the Mean). It also gives the percentage change of the score with respect to the score of the control groups.

TABLE I

| | | Hole-board test | | | | | |
| --- | --- | --- | --- | --- | --- | --- | --- |
| | Dose | DBA-derived strain | | C57 Black Mice strain | | NMRI strain | |
| Compound | (mg/kg) | X ± SEM | % Change | X ± SEM | % Change | X ± SEM | % Change |
| Compound I | 9.5 | 16.1 ± 3.1 | 80.9 | 22.5 ± 3.1 | 47.1 | NT | |
| | 17.0 | 21.5 ± 3.4* | 141.6 | 21.0 ± 2.7 | 37.3 | NT | |
| | 30.6 | 17.1 ± 2.1* | 92.1 | 24.9 ± 3.3* | 62.7 | 29.4 ± 2.8 | −10.1 |
| | Control | 8.9 ± 1.4 | — | 15.3 ± 2.6 | — | 32.7 ± 2.5 | — |
| Compound II | 9.5 | 9.9 ± 1.4 | 0 | | | | |
| | 17.0 | 7.9 ± 2.0 | −20.2 | NT | | NT | |

TABLE I-continued

| | | Hole-board test | | | | | |
|---|---|---|---|---|---|---|---|
| | Dose | DBA-derived strain | | C57 Black Mice strain | | NMRI strain | |
| Compound | (mg/kg) | X ± SEM | % Change | X ± SEM | % Change | X ± SEM | % Change |
| | 30.6 | 10.1 ± 2.7 | 2.0 | | | | |
| | Control | 9.9 ± 2.4 | — | | | | |
| Diazepam | 0.5 | 19.7 ± 2.7* | 45.9 | 33.7 ± 3.0* | 60.5 | 49.8 ± 3.8* | 25.4 |
| | 1.0 | 14.9 ± 3.0 | 10.4 | 42.1 ± 3.4* | 100.5 | 51.1 ± 2.9* | 28.7 |
| | Control | 13.5 ± 1.9 | — | 21.0 ± 3.3 | — | 39.7 ± 2.8 | — |

NT: not treated
(*): significant increase in activity compared with the control group: $P \leq 0.05$; Mann-Whitney U-test The results show that the three strains of mice tested differ from one another by their baseline levels (control tests), which are much higher for the normal NMRI mice than for the other two strains. It is known that the number of holes explored is considerably reduced under the influence of anxiogenic agents, such as caffeine and yohimbine (R. LISTER, Pharmacol. Ther., 46, (1990), 321–340). Consequently, the low level observed for the control groups of unhealthy DBA-derived and C57 Black Mice strains correctly reflects the increased level of intrinsic anxiety in these two strains.

As with diazepam, (S)-(−)-α-ethyl-2-oxo-1-pyrrolidineacetamide considerably increases the score achieved by the DBA-derived and C57 Black Mice strains, but unlike diazepam, compound I has practically no anxiolytic effect on the normal NMRI strain. Diazepam is also very active on the latter strain and the increase in score reflects very well the disinhibition effect which is specific to benzodiazepines. The dependence of the anxiolytic effect of compound I on the nature of the strain, and the pronounced selectivity of this effect for strains which exhibit unhealthy anxiety, suggests that compound I is particularly useful in the treatment of exacerbated emotional states, independently of any disinhibiting effect on the behavior. The (R)-(+)-α-ethyl-2-oxo-1-pyrrolidineacetamide enantiomer (compound II) is inactive on these strains.

2. Four-Plates Test (Punished Behavior)

The general approach used in this type of experiment consists of inducing the inhibition of a specific response by applying a stimulus which produces aversion at the time of that specific response. The "four-plates" test is an easy method described for the first time by J. R. BOISSIER et al., in Eur. J. Pharmacol., 4, (1968), 145–151, for evaluating the potential anxiolytic activity of new compounds in laboratory animals. In a first stage, it involves placing a mouse in an unfamiliar environment, which consists of a surface covered by four metal plates which can be electrified, and during a specific period of time, the number of times that the animal crosses the surface, passing from one plate to another is counted (unpunished crossings). In a second stage, the animal is punished by an electric shock to the paws, each time it crosses right over the surface (punished crossings), which induces on the animal an immobilizing reaction. Under conditions with punishment (punished crossings), the number of crossings over the surface to explore the environment is strongly reduced. On the other hand, the reduction in the number of crossings under conditions with punishment is inhibited in animals which have been previously treated with an anxiolytic agent.

The compounds tested, (S)-(−)-α-ethyl-2-oxo-1-pyrrolidineacetamide (compound I) and chlordiazepoxide, are administered to the animals by intraperitoneal injection (10 ml/kg of mouse) 30 minutes before the beginning of the test. The animals in the control groups receive the carrier only. Table II gives the mean (X±SEM) of the number of crossings made under punished conditions and under unpunished conditions for groups of 30 NMRI mice, over a period of 1 minute and at the doses indicated.

It also gives the percentage change of the score with respect to the score of the control groups.

TABLE II

| | | Four-plates test | | | |
|---|---|---|---|---|---|
| | | Number of crossings | | | |
| | Dose | Punished crossings | | Unpunished crossing | |
| Compound | (mg/kg) | X ± SEM | % Change | X ± SEM | % Change |
| Compound I | 30.6 | 7.8 ± 0.6 | 16.4 | 14.7 ± 0.7 | 3.5 |
| | 54.0 | 8.9 ± 0.6* | 32.8 | 12.7 ± 0.7 | −10.6 |
| | 95.2 | 8.5 ± 0.5* | 26.9 | 13.7 ± 0.6 | −3.5 |
| | Control | 6.7 ± 0.4 | — | 14.2 ± 0.8 | — |
| Chlordiazepoxide | 2.0 | 10.9 ± 0.5 | 18.5 | 17.4 ± 1.0 | 13.7 |
| | 4.0 | 10.9 ± 0.5* | 18.5 | 16.1 ± 0.7 | 5.2 |
| | 8.0 | 13.2 ± 0.6* | 43.5 | 22.7 ± 0.8* | 48.4 |
| | 16.0 | 13.7 ± 0.7* | 48.9 | 22.8 ± 1.0* | 49.0 |
| | Control | 9.2 ± 0.5 | — | 15.3 ± 0.8 | — |

(*): significant increase in activity with respect to the control group: $P \leq 0.05$; Mann-Whitney U-test The results show that, under punished conditions, the number of crossings is lower than under unpunished conditions, both for the control groups and for the treated groups.

Compound I and chlordiazepoxide increase the number of crossings under punished conditions but, unlike compound I, chlordiazepoxide also has the same effect under unpunished conditions by disinhibiting normal behavior.

These results show that (S)-(−)-α-ethyl-2-oxo-1-pyrrolidineacetamide (compound I) offers an advantage over existing drugs because it only exhibits its anxiolytic activity under conditions which induce severe anxiety and not under normal conditions.

This selectivity of compound I enables to distinguish an anxiolytic effect from an effect which would result in an increase of activity per se.

3. Elevated Plus-Maze Test

This test is a simple and rapid method, widely used for detecting the anxiolytic activity of new compounds. Unlike most anxiety tests which use nociceptive stimuli, for example an electric shock, this test relies solely on measuring the spontaneous activity of an animal confronted with a natural anxiogenic situation, which causes a conflict between two opposed tendencies: the desire to explore a novel environment and the desire to flee from an open elevated area. Relative exploration of the open or closed arms of a maze is a reflection of an anxiety state of the animal, exploration of the open arms being strongly reduced in animals that exhibit a high anxiety state (S. PELLOW et al., J. Neurosci. Methods, 14, (1985), 149–167).

An anxiolytic compound increases the number of visits to the open arms and the time spent to explore them, whereas with benzodiazepines, part of this increase has been attributed to induction of stereotypy by the drug at the doses used (U. FALTER et al., Behav. Processes, 29, (1993), 128–129). The technique used in this test is that described by S. PELLOW (loc. cit) modified by R. J. RODGERS et al. (Psychopharmacology, 106 (1992), 102–110). This modification consists of enhancing the anxiety state of the animals, by previously placing them on an elevated maze (pre-test) of which the four arms are open, which has the effect of reducing the number of explorations into the open arms (baseline) when the animal is placed, 24 hours later, on a conventional maze having 2 open and 2 closed arms.

The activities of (S)-(−)-α-ethyl-2-oxo-1-pyrrolidineacetamide (compound I), of the dextrorotatory enantiomer (compound II) and of chlordiazepoxide have been examined using this test. The compounds are administered to Sprague-Dawley rats by intraperitoneal injection (10 ml/kg of rat) 60 minutes before the beginning of the test. The animals in the control group received a saline solution (0.9% NaCl). Table III gives the mean values for the total number of entries into the arms of the maze, the percentage of entries into the open arms with respect to the total number of entries, and the time spent exploring these open arms, for groups of 15 rats (control groups and groups treated with the doses indicated), each in the maze for 4 minutes.

TABLE III

| | | Elevated plus-maze test | | |
|---|---|---|---|---|
| | | Total number | Open arms | |
| Compounds | Dose (mg/kg) | of entries X ± SEM | % entries X ± SEM | Time (sec) X ± SEM |
| Control | | 8.6 ± 1.0 | 10.3 ± 3.0 | 5.2 ± 2.0 |
| Compound I | 17.0 | 11.9 ± 0.7* | 20.2 ± 3.0* | 16.1 ± 3.1* |
| Compound II | 17.0 | 8.3 ± 0.9 | 10.9 ± 3.1 | 5.7 ± 2.2 |
| | 54.0 | 9.2 ± 0.7 | 11.8 ± 2.7 | 6.8 ± 1.6 |
| Chlordiazepoxide | 5.0 | 15.0 ± 1.3* | 27.1 ± 2.7* | 27.1 ± 3.7* |

(*) significant increase in activity compared with the control group: $P \leq 0.05$; Mann-Whitney U-test.

The results show that, for the control group, the number of entries into the open arms only represents a very low percentage of the total number of entries.

Treatment of animals with compound I or with chlordiazepoxide significantly increases the number of entries into the open arms as well as the time spent to explore them. On the other hand, compound II has no activity.

These results confirm the value of compound I in the treatment of pathological anxiety states.

4. Potentiated Startle Test

The startle response to a loud sound (sound aggression) is potentiated by simultaneous presentation of a light stimulus that has been previously paired with an electric shock to the paws of the animals. In this case, the anxiety induced by the combined sound and light aggressions (potentiated startle) originates from the premonition of a painful and unpleasant event (M. DAVIS, Psychopharmacology, 62, (1979), 1–7).

Anxiolytic compounds, such as benzodiazepines or buspirone, reduce the amplitude of the potentiated startle response proportionally to the dose used (S. GREEN et al, "Animal Models of Anxiety" in "Behavioural Models in Psychopharmacology", P. Willner (ed.), Cambridge Univ. Press, 21–49, 1991; M. DAVIS, Trends Pharmacol. Sci., 13, (1992), 35–41). The technique used in this test is based upon that proposed by M. DAVIS (loc. cit.) and comprises essentially two stages:

1st stage: Training—the animals are trained to react to a light stimulus accompanied by an electric shock to the paws;

2nd stage: Main test—the amplitude of the startle response of the animals to a sound aggression accompanied by a light stimulus without electric shock is measured—20 tests—(potentiated startle response or PSR), and the amplitude of the startle response of the animals to sound aggression, neither accompanied by a light stimulus, nor by an electric shock, is also measured—20 tests—(acoustic startle response or ASR).

Groups of 10 male untrained Sprague-Dawley rats are used. The compounds tested are (S)-(−)-α-ethyl-2-oxo-1-pyrrolidineacetamide (compound I) and chlordiazepoxide. They are administered by intraperitoneal injection (1 ml/kg of rat) 60 minutes before the main test. Animals in the control group receive only the saline solution (0.9% NaCl). At the time of the test, each animal is placed in a cage connected to accelerometers which record automatically the startles of the animals and express the amplitude of the response in arbitrary units.

Table IV gives the mean of the amplitudes obtained for ASR and PSR responses at the doses indicated.

TABLE IV

| | | Potentiated startle test | |
|---|---|---|---|
| Compound | Dose in mg/kg | PSR X ± SEM | ASR X ± SEM |
| Control | | 22965 ± 4760* | 17326 ± 3126 |
| Compound I | 17.0 | 14817 ± 3056** | 14388 ± 2214 |
| Chlordiazepoxide | 5.0 | 10393 ± 2079** | 8759 ± 2352** |

(*) Significant difference between PSR and ASR: $P \leq 0.05$, paired t-test
(*) Significant difference between treated and control groups: $P \leq 0.05$; Student's t-test The results for the animals in the control group show that the PSR response is, as expected, more intense than the ASR response. Compound I strongly reduces the amplitude of the potentiated startle response (PSR) but only has a small effect on the acoustic startle response (ASR).

Chlordiazepoxide, on the other hand, attenuates the amplitude of the two responses in a significant manner. The influence of benzodiazepines on ASR illustrates an inherent disadvantage with this class of compounds, which is attributable to their sedative effect.

A compound such as (S)-(−)-α-ethyl-2-oxo-1-pyrrolidineacetamide, which acts specifically on the PSR response, may be predicted as having greater specificity for the treatment of pathological anxiety states and, hence offers an advantage over existing therapies.

5. Neuroendocrine Response to Stress

Adaptive responses to stress, involving negative-feedback control mechanisms in the hypothalamic-pituitary-adrenergic system, are profoundly impaired in the aged rat. These age-related impairments can be demonstrated by measuring the basal plasma corticosterone level, which is much higher in aged subjects than in the young (R. M. SAPOLSKY, Neurobiol. Aging, 13, (1991), 171-174).

A stress situation rapidly increases the plasma corticosterone level both in young and in aged animals but, for the latter, recovery from stress occurs much more slowly and less completely (R. M. SAPOLSKY et. al, Exp. Gerontol., 18, (1983), 55–64; A. M. ISSA, et al, J. Neurosci., 10, (1990), 3247-3254).

The consequences of these age-related effects are important because, while it is true that glucocorticoids are essential for survival and adaptation to various stressors, prolonged exposure to excessive levels of glucocorticoids may be pathogenic for the system.

The test used here is the immobilization test described by R. M. SAPOLSKY (1983, loc. cit.). An animal, placed for 5 minutes in a restrainer adjusted so as to fully immobilize it (immobilization stress), develops an anxiety response which results in a rapid increase in the corticosterone level.

In this experiment, groups of 4 to 8 young (2 months of age) and aged (20 to 21 months of age) Sprague-Dawley rats are used. The treated groups receive 17 mg/kg of compound I or 5 mg/kg of chlordiazepoxide per os, 60 minutes before the immobilization test. The control groups only receive the saline solution (0.9% NaCl). The level of plasma corticosterone is measured before stress, at the end of stress and 30 minutes later, in order to determine the state of recovery of the animals.

Table V gives the mean of the plasma level of corticosterone for each group of animals, measured under these conditions.

TABLE V

Response to an immobilization stress

| Animals/Treatment | Plasma corticosterone level (ng/ml) | | |
|---|---|---|---|
| | basal X ± SEM | at the end of stress X ± SEM | after 30 min X ± SEM |
| Young/Controls | 19 ± 4 | 1333 ± 98 | 163 ± 10 |
| Aged/Controls | 238 ± 60 | 1034 ± 94 | 933 ± 145 |
| Aged/Compound I (17 mg/kg) | 83 ± 21* | 1294 ± 101 | 480 ± 54* |
| Aged/CDP (5 mg/kg) | 78 ± 23* | 1533 ± 128* | 1182 ± 185 |

CDP: chlordiazepoxide
(*) Significant difference compared with the aged/control group of animals: P ≤ 0.05, Student's t-test The results confirm that, in the control groups, the aged rats have a basal level of corticosterone much higher than the young rats. At the end of the stress period, this level increases considerably in both cases, but 30 minutes after the end of the stress period, this level still remains very high in the aged/control animals. Thus, recovery in these animals is slower than in young rats.

In the groups of aged animals which have been treated, either with compound I or with chlordiazepoxide, the basal level of corticosterone is lower than in the group of aged control animals, while being greater than the level in the young control animals.

Stress also increases considerably the level of plasma corticosterone in aged animals, however, the aged group treated with compound I recovers much more rapidly than that treated by chlordiazepoxide, as indicated by the level of corticosterone measured after 30 minutes. This result shows that, contrary to chlordiazepoxide, (S)-(−)-α-ethyl-2-oxo-1-pyrrolidineacetamide has a beneficial action on aged stressed subjects by facilitating physiological adaptation to a stress situation.

6. Syndrome of Withdrawal from Benzodiazepines

The abrupt discontinuation from prolonged therapeutic treatment with benzodiazepines is frequently accompanied by a withdrawal syndrome characterized by a wide range of symptoms due to a physical dependence on the drug, such as trembling, nausea, dizziness or hypertension to quote but a few, as well as usual anxiety symptoms which are intense in man (J. H. WOODS et al., Pharmacol. Rev., 39, (1987), 251–419; M. H. LADER, "Abuse Potential, Tolerance and Dependence on Chronic Anxiolytic Treatment" in "Target Receptors for Anxiolytics and Hypnotics: From Molecular Pharmacology to Therapeutics.", J. Mendlewicz and G. Racagni (eds), Karger, Basel, Vol. 3, (1992), p 46–54).

Based on the observation that withdrawal is associated with anxiogenic stimuli, the use of animal anxiety models for detecting signs of withdrawal in animals has been suggested (M. W. EMMETT-OGLESBY et al., Psychopharmacology, 101, (1990), 292–309).

The anxiogenic response to withdrawal from diazepam has in particular been the subject of studies in the rat, using the elevated plus-maze anxiety test, and is expressed by a significant reduction in the exploration of the open arms (S. E. FILE et al., Psychopharmacology 105, (1991), 578–582).

The same model has been used to study the anxiogenic effect of withdrawal from chlordiazepoxide in mice and to demonstrate the anxiolytic activity of (S)-(−)-α-ethyl-2-oxo-1-pyrrolidineacetamide (compound I) on this syndrome.

Groups of 17 mice (NMRI) were used, split up as follows:
group 1: animals are treated intraperitoneally, twice a day, for 21 days, with increasing doses of chlordiazepoxide ranging from 10 to 40 mg/kg; the last injection is performed 60 minutes before the test;
group 2: withdrawal from chlordiazepoxide takes place 24 hours before the test and the withdrawn animals receive a physiological salt solution;
group 3: the withdrawn animals receive compound I intraperitoneally at a dose of 17 mg/kg;
group 4: the withdrawn animals receive compound I intraperitoneally at a dose of 54 mg/kg.

The control group only receives 10 ml/kg of a physiologic solution. Table VI gives the mean values for the total number of entries into the arms of the maze, the percentage of entries into the open arms with respect to the total number of entries, as well as the mean time spent in exploring the open arms for each group of animals, controls and treated.

TABLE VI

Table VII gives the mean value of the time that the animals of the groups treated at the doses indicated and of the control group, take to find the platform, over 4 successive sessions.

TABLE VII

| | | Water-maze test | | | |
|---|---|---|---|---|---|
| | | Time (sec) to find the platform | | | |
| Compound | Dose (mg/kg) | Day 1 X ± SEM | Day 2 X ± SEM | Day 3 X ± SEM | Day 4 X ± SEM |
| Compound I | 17 | 230 ± 21 | 132 ± 26 | 54 ± 7 | 53 ± 4 |
| | 54 | 230 ± 20 | 88 ± 16 | 53 ± 7 | 35 ± 7 |
| | 170 | 235 ± 34 | 155 ± 41 | 88 ± 28 | 46 ± 6 |
| | Control | 197 ± 18 | 124 ± 15 | 56 ± 5 | 43 ± 6 |
| Chlordiazepoxide | 2.5 | 378 ± 26*** | 288 ± 37* | 217 ± 52 | 128 ± 48* |
| | 5.0 | 307 ± 26 | 274 ± 57 | 195 ± 46 | 201 ± 55** |
| | 10.0 | 404 ± 31*** | 309 ± 54 | 299 ± 48*** | 244 ± 43*** |
| | Control | 241 ± 21 | 198 ± 35 | 116 ± 23 | 62 ± 18 |

*P ≦ 0.05
**P = 0.01
***P = 0.001
Mann-Whitney U-test

Syndrome of withdrawal from benzodiazepines
Elevated plus-maze test

| | | Open arms | |
|---|---|---|---|
| Group of animals | Total number of entries X ± SEM | Number of entries (%) X ± SEM | Time (sec) X ± SEM |
| Control | 13.1 ± 0.4 | 23.9 ± 1.5 | 26.7 ± 2.3 |
| 1 | 22.9 ± 1.0 | 44.0 ± 3.5 | 72.1 ± 6.0 |
| 2 | 9.8 ± 0.6 | 10.1 ± 2.9 | 8.8 ± 3.0 |
| 3 | 12.5 ± 0.7 | 15.5 ± 2.7 | 16.8 ± 4.1* |
| 4 | 12.2 ± 0.5 | 23.5 ± 3.6* | 27.3 ± 5.4* |

(*) Significant increase compared with group 2: P ≦ 0.05; Mann-Whitney U-test.

The results clearly show the anxiolytic activity of chlordiazepoxide in animals chronically treated with this drug (group 1), with respect to the controls, which results in an increase of the number of entries into the open arms of the maze and of the time spent exploring them. Withdrawal (group 2) induces anxiety which manifests itself by a large reduction of these entries, whereas (S)-(−)-α-ethyl-2-oxo-1-pyrrolidineacetamide (compound I), at a dose of 54 mg/kg (group 4), removes the anxiogenic effect of withdrawal from chlordiazepoxide and restores a behavior in the treated animals which is similar to that of the control group.

7. Water-Maze Test

Originally introduced by R. MORRIS (J. Neurosci. Methods, 11, (1984), 47–60), the water-maze test is a learning and memorizing test in which rats learn to escape from water by swimming to a hidden platform located at a fixed point in a large circular pool filled with opaque water.

Since the platform is submersed just beneath the surface of the water, it is invisible, and the animal must learn distal cues in order to find the platform (refuge). The test is sensitive to the anterograde amnesic effect of certain drugs, particularly benzodiazepines such as chlordiazepoxide.

Learning is expressed as the time (in seconds) that the animal takes to find the platform during repeated training sessions over 4 consecutive days. The amnesic effect of a drug results in an increase in the time necessary for the animal to reach the refuge.(N. Mc Naughton et al., Behav. Brain Res., 24 (1987), 39–46). In this test, groups of 8 SPRAGUE-DAWLEY rats are used. The treated animals received compound I or chlordiazepoxide, by oral administration 60 minutes before the test. The control group only receives 5 ml/kg of a physiological salt solution.

The results show that chlordiazepoxide has an amnesic effect on the animals, which manifests itself in a significant increase in the time required to find the platform. In spite of natural learning which results in a reduction in the time required as sessions progress, the amnesic effect of chlordiazepoxide in the treated animals, with respect to the control animals, is still very much apparent on the 4th day. On the other hand, (S)-(−)-α-ethyl-2-oxo-1-pyrrolidineacetamide (compound I), even at the strongest dose (170 mg/kg), does not result in a significant difference of the time required to find the platform with respect to the control group. The compound lacks the anmesic properties of chlordiazepoxide which are undesirable side-effects during the treatment of anxiety with benzodiazepines (J. H. WOODS et al., Pharmacol. Rev., 39, (1987), 251–419).

8. Neurotoxicity

The neurotoxic effects of compound I have been compared with those of diazepam and chlordiazepoxide by means of two tests carried out on mice: Irwin's test and the Rotarod test.

Irwin's test (S. IRWIN, Psychopharmacologia (Berl.) 13, (1968), 222–257) is a systematic observational method of the neurotoxic effects of a drug on the general behavior and the physiologic state of a rodent, rat or mouse. The changes observed for various parameters of the behavior and of the condition of the animal are noted and quantified by means of an arbitrary rating scale ranging from 0 to 8, with respect to the control animals. The compounds are administered intraperitoneally to mice at increasing doses and the animals are observed 5, 10, 30, 60 and 120 minutes after injection.

The Rotarod test consists of evaluating the capacity of a rat or mouse to keep its balance for 60 seconds 3 cm diameter rod which rotates at a speed of 6 rpm (N. W. DUNHAM et al., J. Am. Pharm. Assoc. XLVI, (1957), 208–209). The compounds are administered intraperitoneally to mice at increasing doses 60 minutes before carrying out this test.

Table VIII shows, for Irwin's test, the doses (mg/kg) of the compounds which cause the first perceptible changes in the observed parameters. For the Rotarod test, Table VIII gives the $ED_{50}$ dose (mg/kg) of the tested compounds, that is the dose at which 50% of the tested mice are unable to remain on the rotating rod for 60 seconds.

TABLE VIII

| Parameters | Neurotoxicity | | |
|---|---|---|---|
| | Compound I (mg/kg) | Diazepam (mg/kg) | Chlordiazepoxide (mg/kg) |
| Irwin's test | – | | |
| Reduced spontaneous activity | NE | 0.9 | 10.8 |
| Reduced reactivity to manipulation | NE | 2.8 | 33.5 |
| Impaired vigilance | NE | 2.8 | 33.5 |
| Muscle relaxation | 540 | 0.9 | 3.4 |
| Motor incoordination | NE | 2.8 | 10.8 |
| Impaired righting reflex | 1700 | 2.8 | 6.1 |
| Rotarod test | | | |
| $ED_{50}$ | >1700 | 2.8 | 5.7 |

NE: no effect up to 1700 mg/kg

The results show that the first neurotoxic effects of (S)-(−)-α-ethyl-2-oxo-1-pyrrolidineacetamide (compound I) only appear at very high doses. First symptoms of muscle relaxation appear at 540 mg/kg, and at 1700 mg/kg, the highest dose tested, a disturbance of the righting reflex becomes apparent. The latter dose is up to 100 times greater than the anxiolytic dose.

Diazepam and chlordiazepoxide, on the other hand, reduce activity, reactivity and vigilance and produce muscle relaxation and impaired motor coordination at relatively low doses which are only two to three times higher than the anxiolytic doses.

In animals, compound I thus has a therapeutic margin, between the anxiolytic dose and the neurotoxic doses, which is much greater than that of benzodiazepines.

9. Clinical Test

The anxiolytic activity of (S)-(−)-α-ethyl-2-oxo-1-pyrrolidineacetamide has been tested during an open clinical trial carried out on 76 patients of both sexes, 39 years old in average, and suffering from various types of anxiety: phobias, panic, general anxiety and obsessional disorders.

The compound was administered orally to these patients at an average dose of 250 mg, twice a day, for four weeks. The level of anxiety of the patients was rated by means of the Hamilton anxiety scale (M. HAMILTON, Brit. J. Med. Psychol., 32, (1959), 50–55). The compound was considered active each time a reduction of at least 30% in the level of anxiety was observed.

The compound was shown to be active in 56 patients. Those who responded best to the treatment were those who suffered from anxiety of psychic origin, as opposed to those who were affected by anxiety of psychosocial origin. Some patients occasionally reported somnolence but it was sufficiently light not to be considered as sedation. Indeed, the mental efficiency, attention and memory tests were not affected by the treatment.

We claim:

1. A method for the treatment of anxiety in a patient in need thereof, which comprises administering to said patient an effective amount of (S)-(−)-α-ethyl-2-oxo-1-pyrrolidineacetamide of the formula

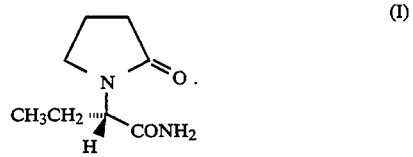

2. A method for the treatment of anxiety caused by acute post-traumatic stress in a patient in need thereof, which comprises administering to said patient an effective amount of (S)-(−)-α-ethyl-2-oxo-1-pyrrolidineacetamide of the formula

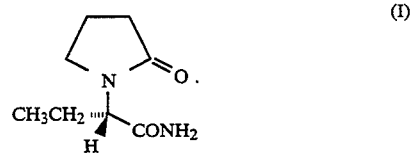

3. A method for the treatment of anxiety induced by the withdrawal from chronic administration of benzodiazepines in a patient in need thereof, which comprises administering to said patient an effective amount of (S)-(−)-α-ethyl-2-oxo-1-pyrrolidineacetamide of the formula

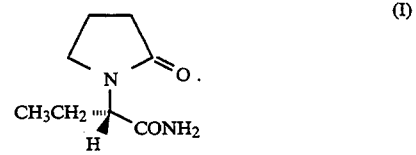

4. The method of claim 1, wherein the effective amount is from 5 to 70 mg/kg per day.

5. The method of claim 2, wherein the effective amount is from 5 to 70 mg/kg per day.

6. The method of claim 3, wherein the effective amount is from 5 to 70 mg/kg per day.

* * * * *